United States Patent [19]
Heissler

[11] Patent Number: 5,186,339
[45] Date of Patent: Feb. 16, 1993

[54] DEVICE COMPRISING A PLURALITY OF RECEPTACLES ARRANGED IN A SINGLE ROW FOR CONTAINERS FILLED WITH A LIQUID

[75] Inventor: Walter Heissler, Wendlingen, Fed. Rep. of Germany

[73] Assignee: Eastman Kodak Company, Rochester, N.Y.

[21] Appl. No.: 732,272

[22] Filed: Jul. 18, 1991

[30] Foreign Application Priority Data

Jul. 20, 1990 [DE] Fed. Rep. of Germany ....... 4023194

[51] Int. Cl.$^5$ .................................................. A47F 7/00
[52] U.S. Cl. ....................................... 211/74; 422/104; 206/443
[58] Field of Search ................. 211/74, 60.1; 422/104; 206/443

[56] References Cited

U.S. PATENT DOCUMENTS

| | | |
|---|---|---|
| 3,379,315 | 4/1968 | Broadwin . |
| 3,604,566 | 9/1971 | Rem et al. ............................. 211/74 |
| 4,124,122 | 11/1978 | Emmitt . |
| 4,453,639 | 6/1984 | Sharma ................................. 211/74 |
| 4,805,772 | 2/1989 | Shaw et al. . |
| 4,826,003 | 5/1989 | Levy . |

FOREIGN PATENT DOCUMENTS 0159346  6/1988  European Pat. Off. .

Primary Examiner—Robert W. Gibson, Jr.
Attorney, Agent, or Firm—Dana M. Schmidt

[57] ABSTRACT

A device for use in an analyzer is described comprising a plurality of receptacles which are arranged in a single row and into which containers of different length and diameter containing a liquid can easily be inserted.

For this purpose, the device is provided with holding elements at different levels along a side for insertable platforms transversing the receptacles and mounting means along the upper edge for an insertable adapter covering the openings of the receptacles.

The holding elements and the mounting means are partly designed as positioning means and/or as latch means. Within the receptacles platform and the bottom in base of device have a ramp and the exterior wall is provided with a recess at the upper edge.

Furthermore, a carrying means comprising a handle with a cam and a support is arranged at an end face of device.

Due to this design of the device, the openings of the containers are aligned in a predetermined position above the upper edge and, thus, containers having differing rims and/or sealing members can easily be scanned and processed. Moreover, the carrying means, in connection with a widened base, guarantees failsafe handling of the containers inside and outside the analyzer.

26 Claims, 6 Drawing Sheets

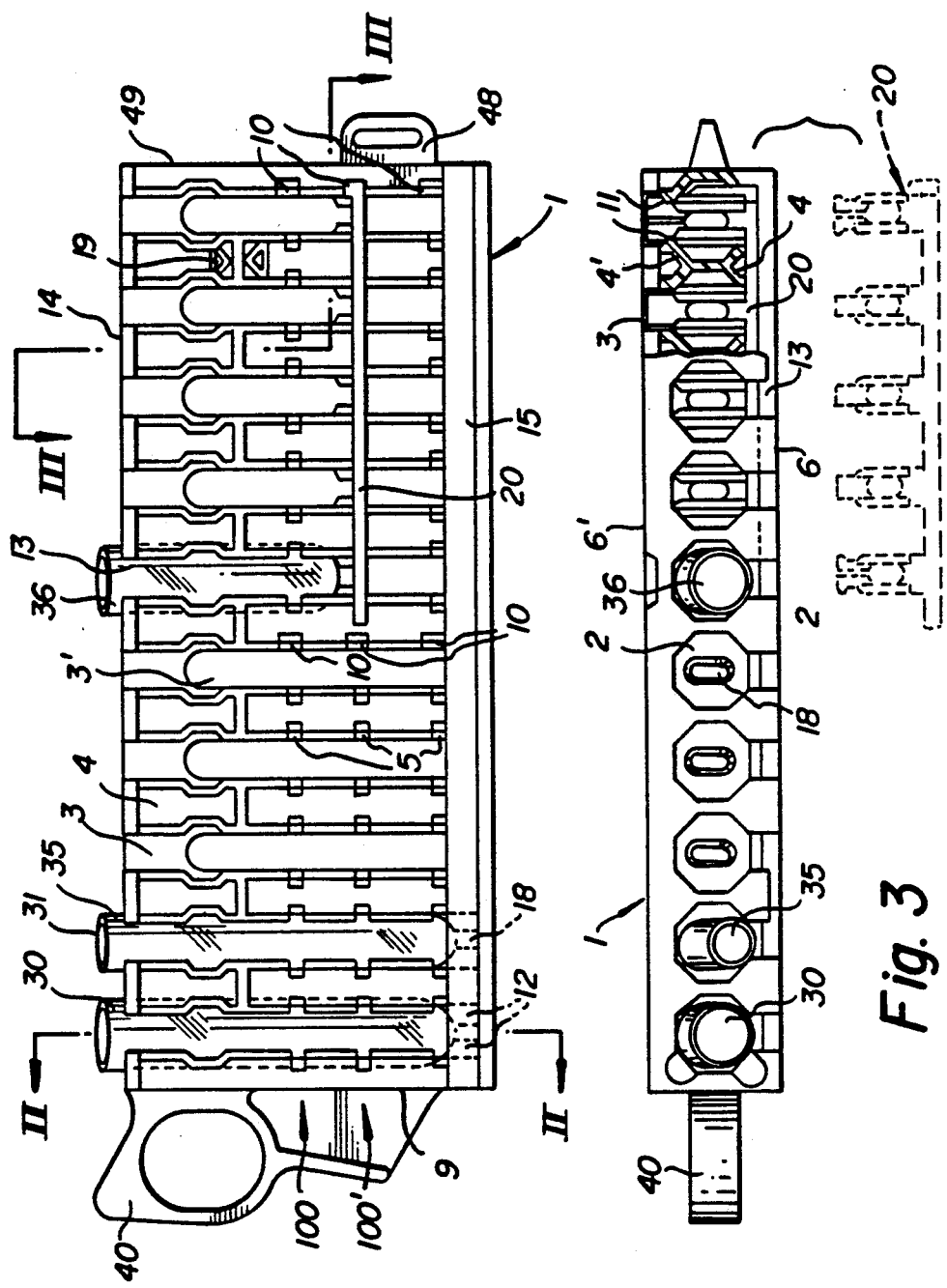

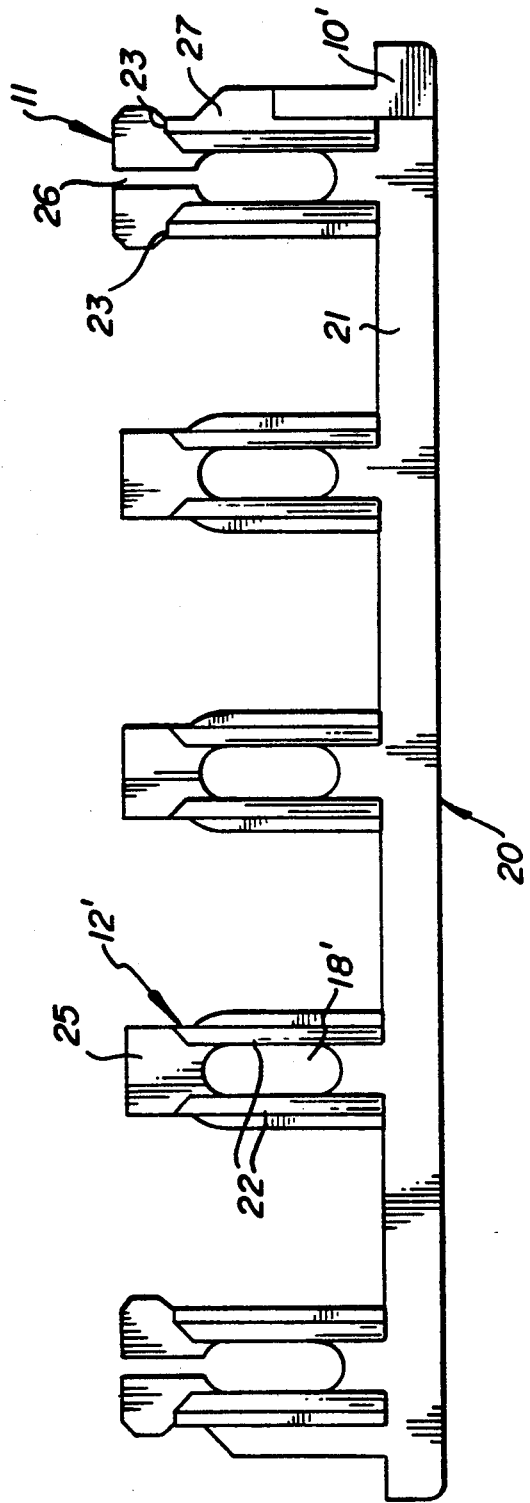
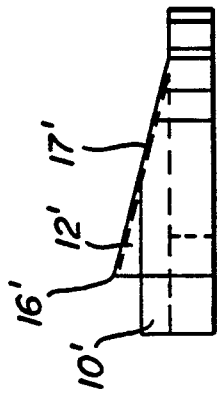
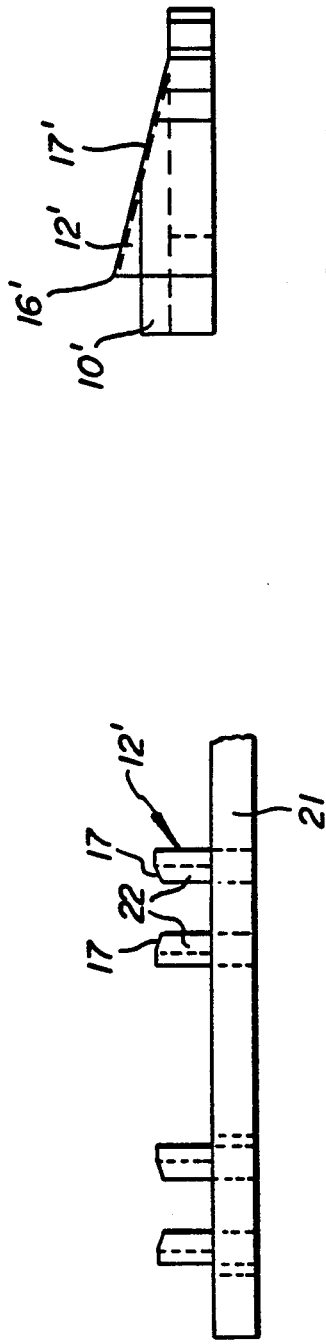

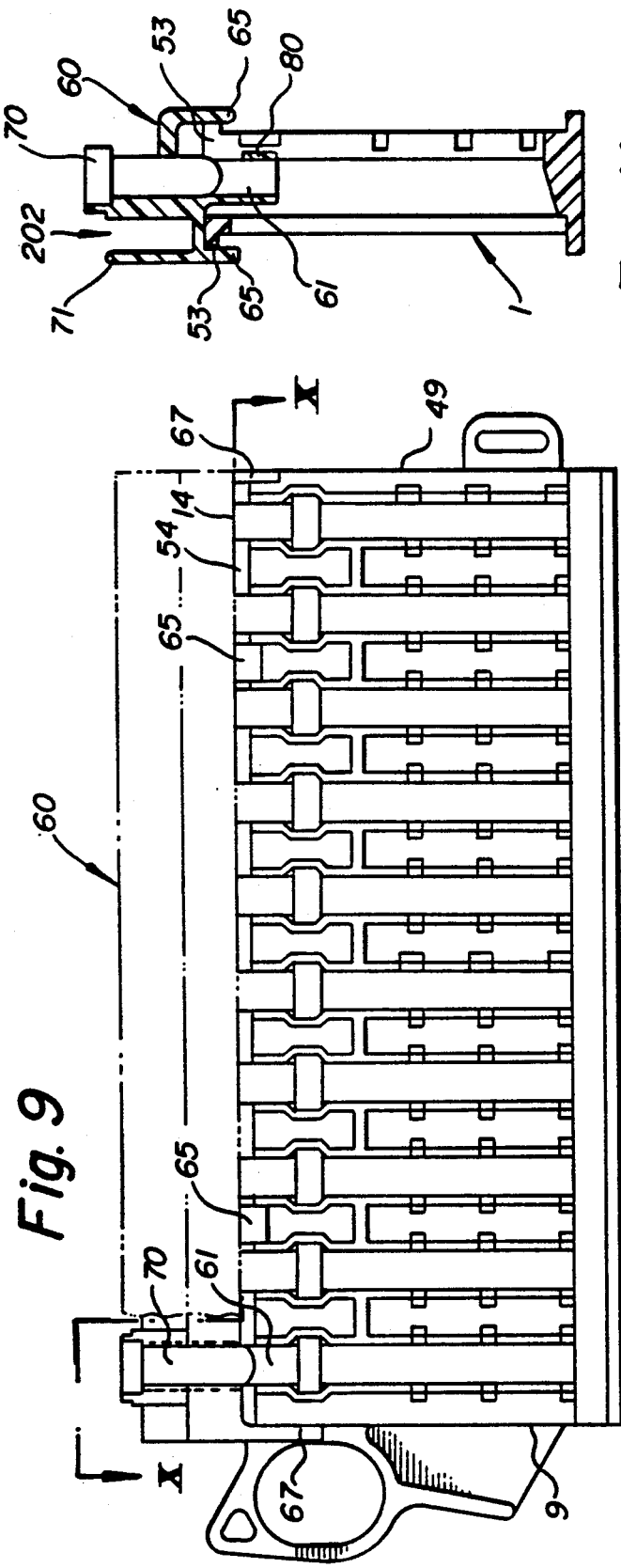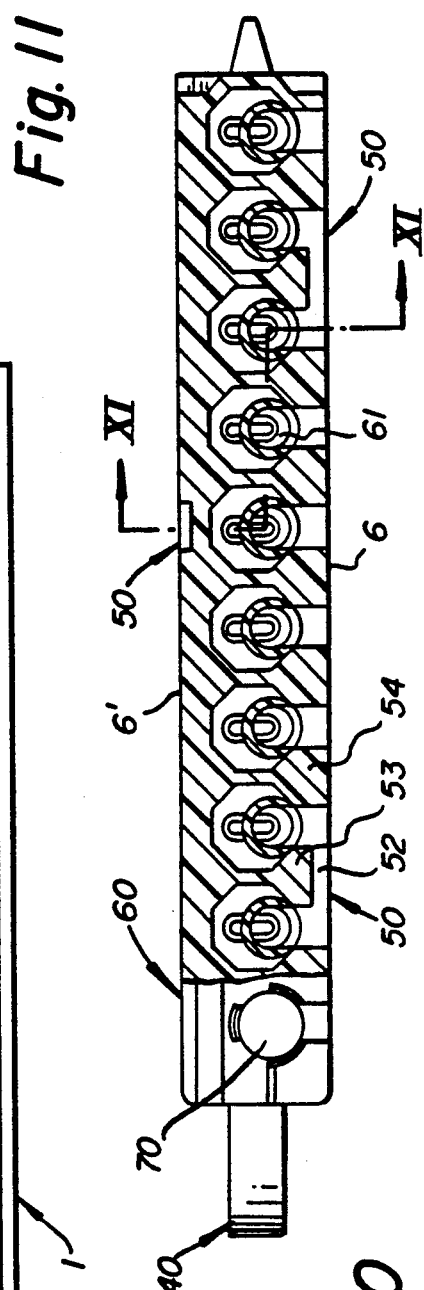

DEVICE COMPRISING A PLURALITY OF RECEPTACLES ARRANGED IN A SINGLE ROW FOR CONTAINERS FILLED WITH A LIQUID

FIELD OF THE INVENTION

The invention relates to a tray for containers of liquid.

BACKGROUND OF THE INVENTION

Devices for holding and transporting containers filled with a liquid are known which are used in an analyzer to process a number of body fluids or samples to be examined.

EP-B-0 159 346 discloses a cassette for holding a plurality of liquid containers arranged in a single row and having different diameters and/or different lengths for transporting the containers to a testing station. The openings of the containers are located at the same level and the containers are centered and fixed by means of a spring element. The containers sealed by stoppers are transported horizontally and for liquid removal are moved to an inclined position in which the stopper points downwards. For removing the liquid, the stopper is pierced by the hollow needle of an aspirator.

It is the object of the invention to provide a device of the generic type permitting easy inserting into and removal of the containers out of the device as well as the use of containers having differing rims and/or sealing members (stopper or cup). Also, removal of liquid, scanning of the containers and removal of stoppers from their openings are to be easily performed and failsafe handling of the containers inside and outside the analyzer is to be warranted.

SUMMARY OF THE INVENTION

The above object is attained in that in a vertically extending arrangement different elements are provided for supporting at least one loose platform transversing the receptacles. In this connection the holding elements can be arranged along one of the sides of device at the exterior wall of the receptacles and define cavities or elevations.

More specifically, in one aspect of the invention, there is provided a device comprising a plurality of connected receptacles aligned in a single row and in which are positioned containers of liquid that are of predeterminedly varying heights and diameters, said receptacles having first bottom wall means for supporting the bottom of containers, and exterior walls provided with apertures for scanning the containers. The device is improved in that it further includes removable second bottom wall means of varying lengths for supporting the bottom of containers of a reduced height, and mounting means in the exterior walls for mounting the second bottom wall means at a plurality of differing, alternative distances above the first bottom wall means so that the second bottom wall means, when mounted, are generally parallel to and above the first bottom wall means.

In accord with another aspect of the invention, there is provided a device comprising a plurality of connected receptacles aligned in a single row and in which are positioned containers of liquid that are of predeterminedly varying heights and diameters, said receptacles having bottom wall means for supporting the bottom of containers, exterior walls provided with apertures for scanning the containers, and an axis extending through said receptacles. The device is improved in that the said bottom wall means are inclined at an angle effective to tilt containers in said receptacles so that such containers are out of plumb and out of alignment with said axis of the receptacles.

Appropriately, the holding means of the platform and the mounting means of the adapter are partly formed as positioning means and/or latch means. Advantageously, both the platform and the bottom surface of the base of the device within the receptacles are formed as a ramp. In the area of the upper edge of the exterior wall a recess is provided which together with the ramp serves for positioning purposes. In an advantageous embodiment of the invention a carrying means is provided comprising a handle, a cam and a support, with the cam being formed as an inclined surface arranged at the upper portion of the handle and the support being provided with a trough and a slope arranged at the lower portion of the handle.

The above object is advantageously attained in that in such a device which is designed as a tray, containers of different height and diameter can easily be placed in the tray on the platform which can be positioned at different levels or in the adapter and removed therefrom. This means that the openings of the containers are aligned in a predetermined position above the upper edge of the tray and, thus, containers having differing rims and/or sealing members can easily be scanned and processed.

Moreover, the advantageously designed carrying means, in connection with a widened base of the tray, guarantees failsafe handling of the containers inside and outside the analyzer.

A detailed description of the device according to the invention will be apparent from the features of the subclaims as well as from the description of an embodiment shown in the drawing.

BRIEF DESCRIPTION OF THE DRAWINGS

FIG. 1 shows a side elevation of the device according to the invention.

FIG. 2 shows a cross-section of the device along the line II—II of FIG. 1,

FIG. 3 shows a top view of the device, sectioned along the line III—III of FIG. 1, FIG. 4 represents a top view of a platform used with the device according to FIG. 1, FIG. 5 represents a fragmentary side elevational view of the platform according to FIG. 4, FIG. 6 represents an end elevational view of the platform according to FIG. 4, FIG. 9 shows a side elevational view of the device according to 1 including an adapter that is partially broken away, FIG. 10 shows a section view of the device according to FIG. 9, taken along the line X—X, FIG. 11 shows a section view of the device according to FIG. 10, taken along the line XI—XI.

DESCRIPTION OF THE PREFERRED EMBODIMENTS

Figure 7:
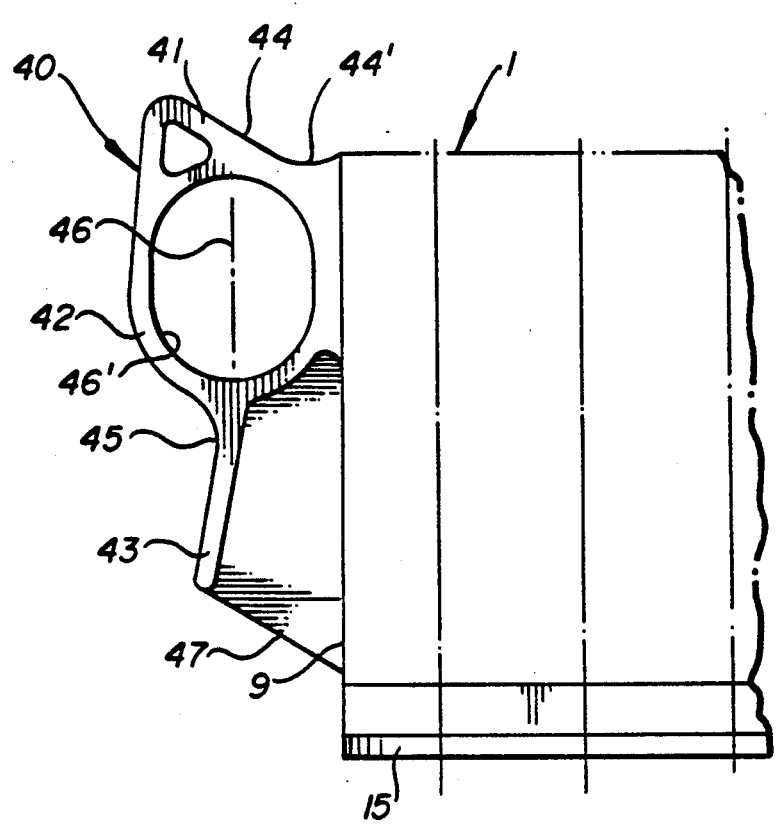
FIG. 7 shows a fragmentary side elevation of the device according to FIG. 1 with a carrying means.
Figure 8:
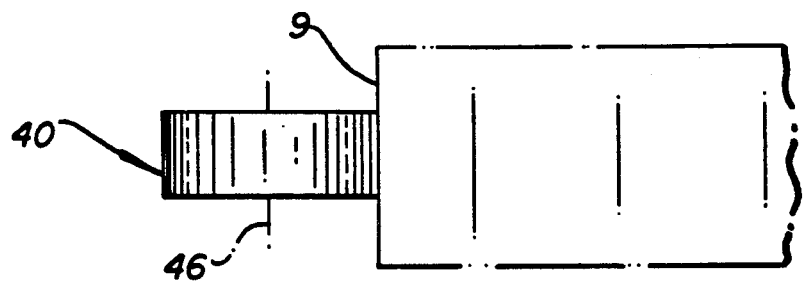
FIG. 8 shows a fragmentary top view of the device according FIG. 7.

Descriptive terms such as "up", "vertical", and "plumb" refer to orientations that occur during normal use of the invention.

A tray 1 shown in FIGS. 1, 2 and 3 consists of a plurality of receptacles 2 arranged in a single row for holding containers 31, 35, of a base 15, a carrying means 40 at an end face 9 and an eyelet-shaped entrainment member 48 at the opposed end face 49.

Receptacles 2 are enclosed by walls and have an octagonal cross-section. At the exterior walls 4 and 4' of the receptacles 2 extending along the two sides 6 and 6' of the device 1, mounting means comprising holding elements 5 are arranged for one or several platforms 20. The holding elements 5 shaped as cavities 7 are arranged at three different levels along a side 6 of tray 1. In the area of the end face 49 and in the central portion of tray 1 the holding elements 5 are vertically arranged and have wider slots so as to form positioning means 10 for the platform 20. Platforms 20 act as alternative bottom walls to support the bottoms of containers 36, or any other containers having a height that is reduced, compared to the height of container 35. As such, platforms 20 provide a rigid support when inserted—that is, the reduced—height containers cannot be pushed through them.

Because the reduced height containers 36 come in standard discrete heights that are predetermined, holding elements 5 are located at heights above base 15 that accommodate these discretely different heights of containers. Conveniently, indicia can be placed at the various heights of holding elements 5, e.g., at 100, 100', to indicate the size (and thus height) of container used with that platform.

Latch means 11, which in the area of the apertures 3 at the outer edges of the exterior walls 4 are designed as depressions, are associated with said positioning means 10 and are arranged on the opposite side 6'. The latch means, thus, are used for holding and, in addition, for supporting a platform 20 transversing the receptacles 2.

The apertures 3 and 3' formed in the exterior walls 4 and 4' of the receptacles 2 are designed as vertically extending slots starting in the area of base 15. At the side 6' of tray 1 they end below the upper edge 14 and at the opposite side 6 they extend through the upper edge 14. At the upper edge 14, each of the apertures 3 is provided with a recess 13 adapted to the different diameters of the various containers 31, 35, 36.

The widened apertures 3 arranged beneath the recesses 13 are intended for scanning the containers 30, 35, 36 by an automatic scanning means. Furthermore, the apertures 3 and 3' provided with index marks arranged on the exterior walls 4 and 4' are used for visually detecting the liquid level within the containers.

The base 15 of tray 1 has a lower section which measured across the longitudinally extending exterior walls 4 and 4' is wider than the receptacles 2. The wider section of base 15 serves to increase stability and to guide and retain device 1 on a trans-port path in an analyzer.

In the upper section of base 15 serving as a support a ramp 12 is arranged in each receptacle 2. The higher edge 16 of ramp 12 faces recess 13 in the exterior wall 4 and along the central axis of its inclined surface 17 the ramp 12 has a slot-shaped opening 18 with the upper edge being chamfered. The opening and the chamfered edge are adapted to shape and size of the bottom of a container.

When a container 31 or 35 is placed in receptacle 2, ramp 12 effects a lateral tilt of the container towards the recess 13 at the upper edge 14 of exterior wall 4 so that the upper portion of the container 31 or 35 is centered and clamped in recess 13 and its lower portion between ramp 12 and the exterior wall 4'. Each container is then tilted out of the vertical axis 30 of device 1, FIG. 2. This facilitates insertion and removal of the containers 30 or 35 and fixes them in tray 1 in a defined and stable position for subsequent transport.

The octagonal cross-section of receptacle 2 permits an additional centered position of container 30, 35 which is opposite to the first position and taken when a container is present in one of the processing stations.

FIGS. 4, 5 and 6 show a platform 20 adapted to the structure of tray 1 according to FIGS. 1, 2 and 3.

Platform 20 consists of a connecting member 21 of rectangular cross-section which on one side is provided with a plurality of ramps 12' at a distance corresponding to that of the individual receptacles 2 of tray 1. The higher edge 16' of ramp 12' faces the connecting member 21. Ramp 12' is comprised of two ribs 22 arranged on a base plate 25 having a slot-shaped opening 18' with shape and dimensions corresponding to ramp 12 in base 15 of tray 1.

The two exterior ramps 12' comprise latch means 11' having detents 23 and a slot 26 at the outer end of each base plate 25. Furthermore, the two base plates 25 are provided with outwardly directed lateral guide surfaces 27 extending beyond connecting member 21. On its upper side, one of said guide surfaces 27 has a positioning means 10' also extending beyond the adjacent protruding end portion of connecting member 21.

Platform 20 is used when the openings 31 of containers 36 which are lower in height than the containers 30 and 35 are to be aligned to a predetermined level above the upper edge 14 of tray 1, which is required for processing (see FIG. 1). For this purpose, one or two platforms 20 are inserted in the holding elements 5 of tray 1 at the level required. Ramp 12' of platform 20 thereby penetrates the apertures 3, 3' and is positioned in the receptacle 2 normal to the longitudinal axis thereof, with the detents 23 engaging with the depressions of latch means 11 and the connecting member 21 abutting at the bottom of the holding elements 5.

Correct and secure position of platform 20 is guaranteed by the positioning means 10, 10'. Also the guide surfaces 27 facilitate insertion of platform 20, which occurs from only one side (4') of device 1 as shown in phantom, FIG. 3.

Figure 15:
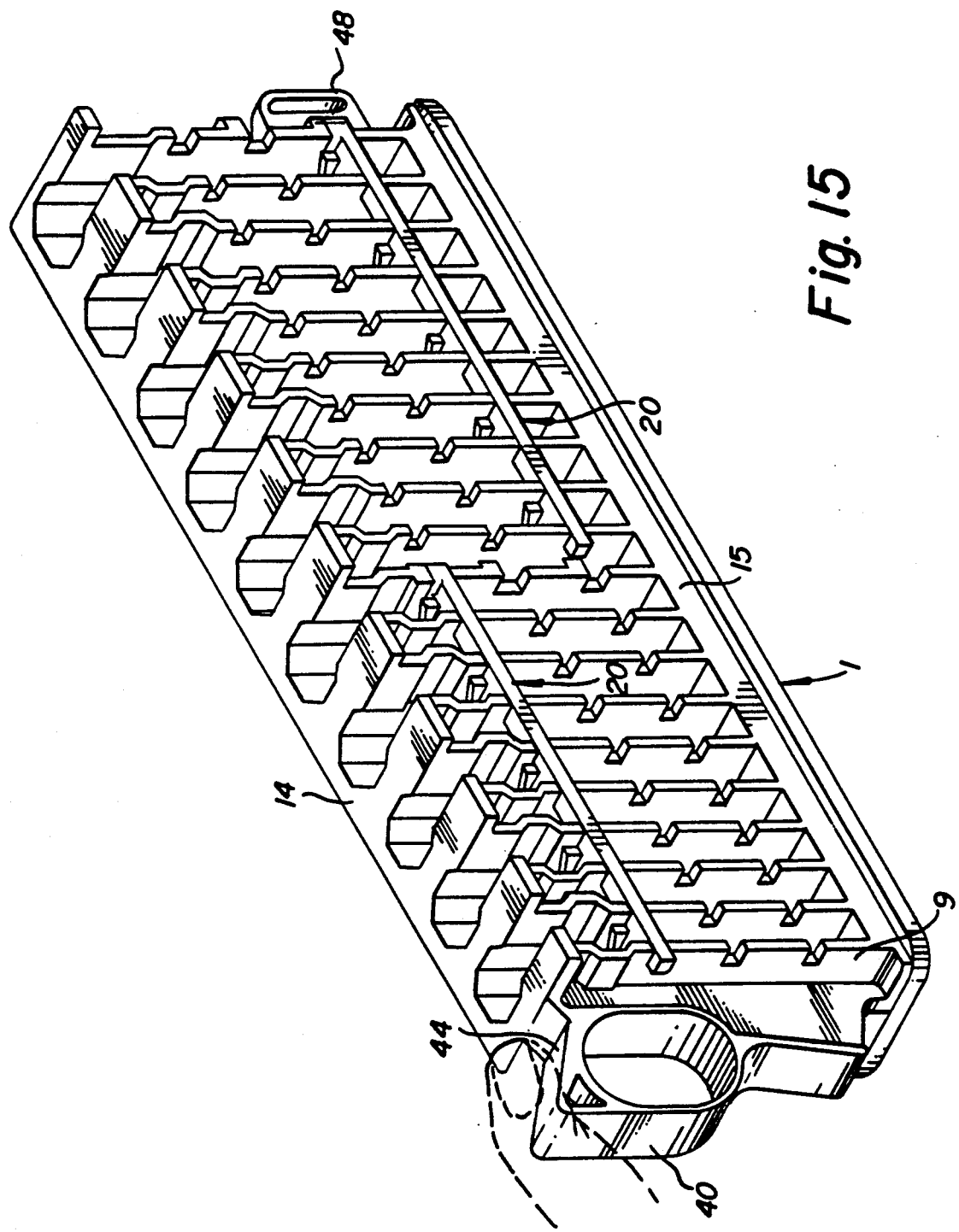
FIG. 15 shows a perspective view of the device according to the invention, wherein more than one platform is in place at a time in the device.

More than one platform 20 can be inserted at a time into the device 1, FIG. 15, preferably at two different heights to allow containers of two different heights to be carried.

The carrying means 40 of tray 1 shown in FIG. 7 is comprised of a cam 41, a handle 42 and a support 43. It is arranged in the upper area of end face 9 of tray 1 and in alignment with the central vertical axis 30 of the device, with the center axis 46 of handle 42 extending horizontally and transversely with respect to the central axis of device 1.

Cam 41 is arranged at the upper end portion of handle 42 and support 43 at the lower. Cam 41 has an inclined surface 44 whose lower end is connected with the upper edge 14 of tray 1 via a trough-shaped section 44'. The upper end of cam 41 is rounded off and changes over into the outer surface of handle 42. Support 43 is connected to handle 42 by means of a trough 45. Slope 47 extends between the lower end of trough 45 and the upper edge of base 15. Slope 47 and inclined surface 44 are provided for easy manual removal of tray 1 from the analyzer with a retaining means in the tray track of an input station having to be overcome. That is, surface 44 is a thumb ramp, FIG. 15, and slope 47 is a finger ramp.

Slope 47 is designed as a narrow web, whereas cam 41, handle 42 and support 43 are somewhat wider.

The dimensions of the components such as cam 41, handle 42 and support 43, render carrying tray 1 adapted to the anatomy of the human hand to assure reliable and easy handling of tray 1. In particular, width, radii and shape of the components mentioned as well as the diameter of the handle are adapted to the dimensions of the thumb, the forefinger and the middle finger. The forefinger extends through aperture 46 of handle 42, FIG. 7.

FIGS. 9, 10 and 11 show an adapter 60 for holding small containers 70 which is placed on tray 1 and fixed thereon, with the receptacles 62 of adapter 60 being associated with the receptacles 2 of tray 1 so as to be in alignment therewith, and the adapter completely covering the device. For this purpose, mounting means 50 are provided in the form of rectangular recesses 52 and projections 53 on the upper edge 14 of tray 1 at the outwardly projecting rim 54. Such small containers can be so-called micro-collection tubes of, e.g., 0.75 ml.

Downwardly extending and projecting latch means 65 are provided on adapter 60 which are associated with the mounting means 50. At the lower end of their inner surfaces, the resiliently designed latch means 65 have latching nipples 66 engaging with the projections 53 of mounting means 50 from below.

The mounting means 50 are arranged unsymmetrically at the rim 54 such that one of the mounting means 50 is provided in the center of the side 6' and two mounting means are provided outside the center on the side 6 of tray 1.

At the end faces of the adapter 60 guides 67 are arranged which project beyond the end faces 9 and 49 of tray 1, with the guides 67 arranged on the end face 9 extending on both sides of the carrying means 40.

Such arrangement of the mounting means 50 latch means 65 and guides 67 assure correct and secure placement of adapter 60. In addition, the guides 67 permit the adapter 60 to be placed on a support surface.

Figure 12:
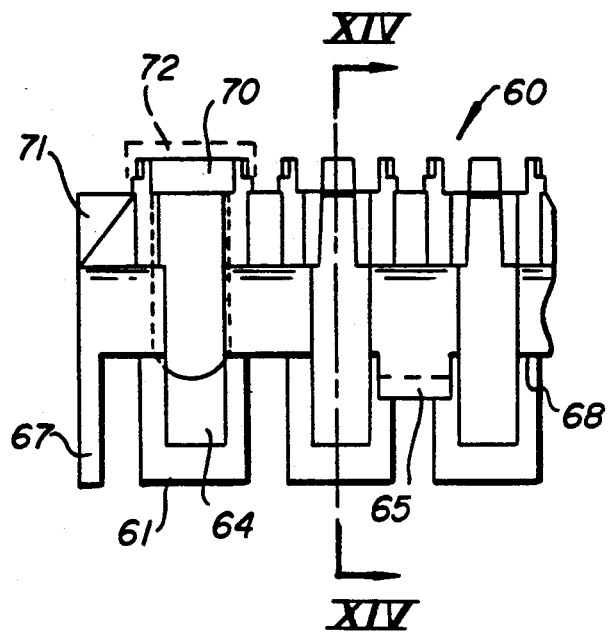
FIG. 12 shows a partial view of FIG. 9 and represents an adapter for a device according to FIG. 1.
Figure 14:
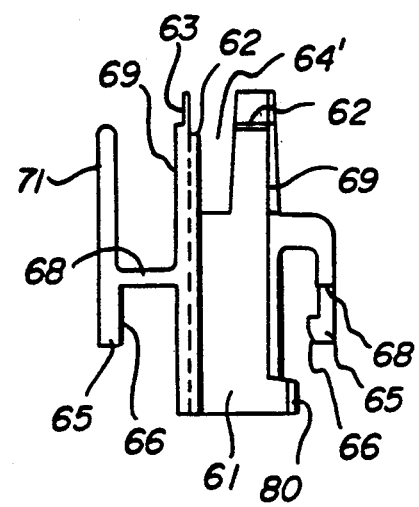
FIG. 14 shows a section view of the adapter according to FIG. 12, taken along the line XIV—XIV.
Figure 13:
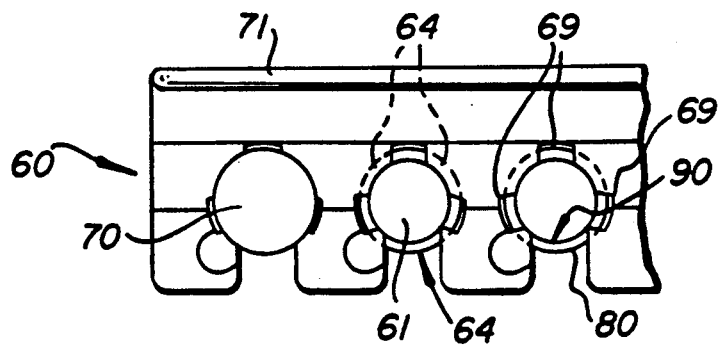
FIG. 13 shows a top view of the adapter according to FIG. 12.

FIGS. 12, 13 and 14 show the adapter 60 as an individual part. Supplementing the features described in FIGS. 9, 10 and 11, the adapter 60 shows that the receptacles 61 are designed as hollow cylinders, are vertically aligned in a row on a support plate 68. The receptacles 61 downwardly project beyond the support plate 68 of adapter 60 to the extent that their end portions are positioned in the area of the widening of the apertures 3 of tray 1 when the support plate 68 rests on tray 1.

On side 6 of tray 1 apertures 64 are provided in each of the receptacles 61 in the form of a vertically extending slot which starts above the lower edge of the receptacle and within the widening of the aperture of tray 1 and extends as far as the upper edge of receptacle 61. Two additional apertures 64' are provided in the form of vertical slots which start above support plate 68 and also extend as far as the upper edge of receptacle 61. With respect to apertures 64, apertures 64' are offset by an angle of 120° so as to form three tongues 69. In the area of the upper edge each tongue 69 is provided with a supporting means 62 within the receptacle 61 which means is designed in the form of a shoulder provided within the upwardly widening opening of receptacle 61. At the level of supporting means 62, the inner diameter is adapted to an upper rim of the cylindrical small container 70 which protrudes to a larger extent. In addition, the wall thickness of the end portions of the tongues 69 decreases inwardly above the supporting means 62, thus said end portions forming resilient centering/fixing means 63.

The exterior shoulder of the centering/fixing means 63 is designed such that a lid 72 can be placed over it and the small containers 70 can be covered to protect the body fluids against fouling and evaporation.

Furthermore, this design of the receptacles 61 permits the small containers 70 to be easily inserted and removed and securely to be transported by means of the adapter 60 or the tray 1 within and outside an analyzer. Aperture 64 in receptacle 61 additionally serves for scanning the small containers 70 and the lower end portion of receptacle 61 is used for scanning the adapter 60. At the outer face of adapter 60 and spaced from the receptacles 61 a wall 71 is provided which is associated with the side 6' of tray 1. Wall 71 protects the small containers 70 and their tethered lids 72 against inadvertent contact when the adapter is manually handled, and also serves for stowing a tab arranged on the lid 72.

The bottom of adaptor 60 preferably includes a closed ring 80 which protrudes sufficiently far, arrow 90, FIG. 13, as to be detectable by a sensing probe that penetrates the aperture 3' of device 1. The protuberance of ring 80 extends beyond where a container 31 or 35 would sit, if present, thereby causing a signal to be generated indicating that adaptor 60 is present.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In a device comprising a plurality of connected receptacles aligned in a single row and in which are positioned containers of liquid that are of predeterminedly varying heights and diameters, said receptacles having first bottom wall means for supporting the bottom of containers, and exterior walls provided with apertures for scanning the containers;

the improvement wherein said device further includes removable second bottom wall means of varying lengths for supporting the bottom of containers of a reduced height, and mounting means in said exterior walls for mounting said second bottom wall means at a plurality of differing, alternative distances above said first bottom wall means so that said second bottom wall means, when mounted, are generally parallel to and above said first bottom wall means.

2. A device as defined in claim 1, wherein said mounting means comprise indentations in only one of said exterior walls, said second bottom wall means including a support constructed to slip into and out of engagement with said indentations at said one exterior wall only.

3. A device as defined in claim 1 or 2, wherein said mounting means are spaced away from said first bottom wall means by distances effective to ensure that containers of said predetermined varying height can all be positioned with openings approximately at the same level.

4. A device as defined in claim 2, wherein said indentations are spaced apart within said one exterior wall in a direction parallel to said first bottom wall means, a distance that is less than the shortest length of said second bottom wall means.

5. A device as defined in claim 2, and further including in said second bottom wall means, for latching onto an exterior wall of said device opposite to said one exterior wall.

6. A device as defined in claim 1 or 2, wherein said first bottom wall means are inclined at an angle effective to tilt containers in said device out of plumb.

7. A device as defined in claim 6, wherein said second bottom wall means are shaped, and said mounting means are constructed, to dispose said second bottom wall means when mounted in said device, at said effective angle.

8. A device as defined in claim 7 wherein said one exterior wall includes said apertures, and each of said apertures is a slot generally aligned with and open into one of said receptacles, and each of said angled bottom wall means is disposed with its highest edge adjacent to said one exterior wall.

9. A device as defined in claim 6 wherein said one exterior wall includes said apertures, and each of said apertures is a slot generally aligned with and open into one of said receptacles, and said angled bottom wall means are disposed with the highest edge adjacent to said one exterior wall.

10. A device as defined in claim 1 or 2, wherein at least said bottom wall means include an opening within each of said receptacles that is shaped and sized to receive and hold a bottom end of a container.

11. A device as defined in claim 10, wherein said second bottom wall means include openings disposed to align with each of said receptacles occupied by said bottom wall means when mounted, that are shaped and sized to receive and hold a bottom end of a container.

12. A device according to claims 1 or 2, wherein the cross-section of the interior of each receptacle has a polygonal shape.

13. A device as defined in claim 1 or 2, and further including carrying means comprising a handle at one end of said device, said handle including a thumb ramp with a surface inclined at an angle to said first bottom wall means.

14. In a device comprising a plurality of connected receptacles aligned in a single row and in which are positioned containers of liquid that are of predeterminedly varying heights and diameters, said receptacles having first bottom wall means for supporting the bottom of containers, and exterior walls provided with apertures for scanning the containers;

the improvement wherein said device further includes carrying means for manually carrying said device, said carrying means comprising a handle at one end of said device, said handle including a thumb ramp with a surface inclined at an angle to said first bottom wall means.

15. A device as defined in claim 14, wherein said handle includes a finger aperture having an axis extending transversely to the vertical axis of the device.

16. A device as defined in claim 14, and further including at an end of the device opposite to said one end, an eyelet-shaped latching member for machine engagement.

17. A device as defined in claims 14, and further including loose adaptors for small containers and a plurality of adaptor-mounting means for mounting said adaptors at the top of the openings to said receptacles.

18. A device as defined in claim 17, wherein said adaptor-mounting means include latch means for removably attaching to said device.

19. A device as defined includes 17, wherein said adaptors have receptacles inserted into and in alignment with said device receptacles.

20. A device as defined in claim 19, wherein said adaptor receptacles have apertures sized to allow scanning of said small containers inside said loose adaptors.

21. A device as defined in claim 19, wherein said receptacles include means for centering and supporting small containers within said adaptor receptacles.

22. A device as defined in claim 21, wherein said centering and support means comprise resilient tongues annularly arranged.

23. A device as defined in claim 18, wherein said adaptor-mounting means include guide members at opposite ends of said adaptor-mounting means, said guide members being asymmetrically configured and disposed to ensure that said adaptor-mounting means will fit onto said device with only one orientation.

24. A device as defined in claim 17, and further including at the bottom of said adaptor, signal-generating means for generating a signal to a sensor indicative of said adaptor being present.

25. A device as defined in claim 24, wherein said signal-generating means comprise a closed ring occupying a portion of each of said device receptacles.

26. In a device comprising a plurality of connected receptacles aligned in a single row and in which are positioned containers of liquid that are of predeterminedly varying heights and diameters, said receptacles having bottom wall means for supporting the bottom of containers, exterior walls provided with apertures for scanning the containers, and an axis extending through said receptacles, the improvement wherein said bottom wall means are inclined at an angle effective to tilt containers in said receptacles so that such containers are out of plumb and out of alignment with said axis of the receptacles.

* * * * *

UNITED STATES PATENT AND TRADEMARK OFFICE
CERTIFICATE OF CORRECTION

PATENT NO. : 5,186,339
DATED : February 16, 1993
INVENTOR(S) : Walter Heissler

It is certified that error appears in the above-identified patent and that said Letters Patent is hereby corrected as shown below:

Column 8, claim 19, line 23, delete "includes 17," and substitute therefor --in claim 17,--

Column 8, line 35, claim 23, delete "18" and substitute therefor --17--.

Signed and Sealed this

Twelfth Day of April, 1994

Attest:

BRUCE LEHMAN

Attesting Officer

Commissioner of Patents and Trademarks